(12) United States Patent
Michot et al.

(10) Patent No.: US 6,228,942 B1
(45) Date of Patent: May 8, 2001

(54) SURFACE MODIFIED CARBONACEOUS MATERIALS

(75) Inventors: Christophe Michot, Grenoble (FR); Michel Armand, Montreal (CA); Michel Gauthier, La Pairie (CA); Yves Choquette, Sainte-Julie (CA)

(73) Assignees: Hydro-Quebec, Montreal (CA); Centre National de la Recherche Scientifique, Paris (FR)

(*) Notice: Subject to any disclaimer, the term of this patent is extended or adjusted under 35 U.S.C. 154(b) by 0 days.

(21) Appl. No.: 09/125,798
(22) PCT Filed: Dec. 30, 1997
(86) PCT No.: PCT/CA97/01008
   § 371 Date: Dec. 2, 1998
   § 102(e) Date: Dec. 2, 1998
(87) PCT Pub. No.: WO98/29358
   PCT Pub. Date: Jul. 9, 1998

(30) Foreign Application Priority Data

Dec. 30, 1996 (CA) .................................................. 2194127
Mar. 5, 1997 (CA) .................................................. 2199231

(51) Int. Cl.$^7$ ................................. C08F 8/28; H01B 1/06; C08K 3/04
(52) U.S. Cl. ........................... 525/183; 525/66; 525/263; 252/511; 524/495; 524/496; 428/367
(58) Field of Search ........................... 525/183, 66, 263; 252/511; 524/495, 496; 428/367

(56) References Cited

U.S. PATENT DOCUMENTS 4,714,569 * 12/1987 Nishino et al. ....................... 252/511

FOREIGN PATENT DOCUMENTS

0289624 * 11/1988 (EP) .
0475075 *  3/1992 (EP) .
0753548 *  1/1997 (EP) .
01152165 *  6/1989 (JP) .

* cited by examiner

Primary Examiner—James J. Seidleck
Assistant Examiner—Olga Asinovsky
(74) Attorney, Agent, or Firm—Oblon, Spivak, McClelland, Maier & Neustadt, P.C.

(57) ABSTRACT

Grafting a polymer at the surface of a carbonated material containing carboxyl amine and/or hydroxyl functions at its surface. This material is suspended in a solution comprising the polymer to be grafted, which includes a carboxyl amine and/or hydroxyl function, the solution also comprising a solvent of the polymer. This is followed by a treatment causing dehydration into a carboxyl function, an amide and/or hydroxyl function and the polymer is thus grafted on the carbonated material by means of ester or amide bonds. Utilization in the cathode or anode of an electrochemical generator, in a polymer material with low polarity, in an ink, and as a conductive deposit on flexible plastic used as electrical contact, electromagnetic protection and antistatic protection.

30 Claims, 4 Drawing Sheets

Cathode: V$_2$O$_5$ + grafted carbon (e = 89 μm)
Current collector: stainless steel (e = 2 mm)
Anode: metallic lithium (e = 50 μm)
Polymer electrolyte: POE/LiTFSI 15/1 (e = 50 μm)

- Carbon deposit on aluminum
- Cathode: $V_2O_5$/carbon/POE–LiTFSI
- Current collector: stainless steel
- Anode: metallic lithium
- Polymer electrolyte: POE/LiTFSI 15/1

SURFACE MODIFIED CARBONACEOUS MATERIALS

TECHNICAL FIELD

The present invention relates to a new process for grafting polymers at the surface of carbonated materials and to the application of materials thus obtained as an electronically conductive additive, in particular in electrochemical generators, as electronically conductive deposit, or as an ink.

PRIOR ART

Carbonaceous materials play a major part in many fields, for example: structural elements (composite material based on carbon fibres, . . . ), pigments (ink, toner, paint, . . . ), electrodes (double layer capacitance, electrolysis of aluminum, . . . ), ion exchangers (removal of heavy metals, purification of water, . . . ), catalyst supports (combustible material battery, . . . ), mineral charges (rubber industry, tire, . . . ), . . .

This wide range of applications is inherent to the specific physico-chemical properties of carbonaceous materials: heat resistance, good electrical conductivity, wide range of specific surface (typically of the order of $m^2/g$ to thousands of $m^2/g$), coloring power, . . .

Among all the physico-chemical parameters characterizing a carbonaceous material one of the most important is the state of its surface which conditions, in final analysis, the interface between the carbonaceous material and the surrounding medium. It is thus well known that various functional groups may be present at the surface of a carbonaceous material or may be introduced later on during its synthesis through different processes: chemical (oxidation, sulfonation, . . . ), physico-chemical (electrolytic treatment, plasma, . . . ) or thermal.

It is thus possible to introduce various functions at the surface of carbonaceous materials: radicals, carbanions, carboxylic acids, sulfonic acids, phosphonic acids, hydroxyls, amines, pyridines, halogens, anhydrides, lactones, pyrones, quinones, etc. The concentration of these different groups at the carbon surface varies typically from 0.1 to 10 meq/g of carbon. It is therefore possible to control and finally modify the surface properties of these materials, for example their acid-base character or their hydrophilic-hydrophobic character. Reference will be made in this connection to the work of I. N. Ermolenko, I. P. Lyubliner & N. V. Gulko: Chemically Modified Carbon Fibers, VCH Publishers Inc., New York, 1990. Thus, carbon powders carrying carboxyl functions at their surface find an important outlet in the field of pigments for high capacity ink jet printers (see Technical Notice Degussa AG: "Pigmentru$\mu$e/ Pigment Blacks").

The possibilities of functionalizing a carbonaceous material are thus sufficiently varied to consider initiating numerous chemical reactions from its surface. Among all the opportunities to modify the interface properties, grafting of polymers is of particular interest For example, the presence of various ultrafine particles (carbon, titanium oxide, silica, ferrite, . . . ) at the surface of a grafted polymer enables to improve the dispensability of the materials thus modified in organic solvents or in suitable polymer matrices. It is thus possible to obtain colloidal dispersions of a carbon whisker which are very stable in tetrahydrofurane by grafting at their surface$\approx$1 g of polystyrene per gram of carbon (N. Tsubokawa, T. Yoshihara, Y. Sone, *J Polym. Sci., Part A, Polym. Chem.*, Vol. 30, 561–567,1992).

Different strategies of synthesis were used for grafting polymers at the surface of a carbonaceous material. Two large families may be mentioned: initiation of polymerization of a monomer from a functional group which is present at the carbon surface, and grafting of a prepolymer containing at least one chemical function capable of reaction with the surface of carbon.

In the first case, a number of works were concentrated on initiating the anionic, cationic or free radical polymerization of monomers, more often by modifying a functional group which is present on a carbonated material to make it active towards the type of polymerization under consideration. Let us mention for example the possibilities offered from a carboxylate function which is easily introduced by oxidation of a carbonated material: transformation into an alkaline metal salt (Li, Na, K. Cs, Rb, . . . ) for anionic polymerization, transformation into an acylium salt (acylium perchlorate, acylium antimony hexafluoride, . . . ) for cationic polymerization or the transformation into peroxyesters for free radical polymerization.

In the second case, other works dealt with the grafting of prepolymers containing a chemical function which is capable of reacting with a group which is present at the carbon surface, most of the time by modifying the group present on the carbon atom to make it reactive. Let us mention for example the possibilities offered by the transformation of carboxyl functions into isocyanate, epoxide, acid chloride, . . . thus enabling grafting of, for example, a polyethylene glycol a polyvinyl alcohol a polyethylene imine, a silicon diol a silicon diamine, . . .

These different processes of synthesis are not completely satisfactory, because they necessitate the chemical modification of the group which is fixed on the carbon atom and/or the polymer which is intended to be grafted makes these synthesis complex and costly to operate on a large scale. Moreover, graftings initiated by polymerization cause a problem of chain endings whose posterior reaction may be unfavourable to the operation of systems integrating these carbonated materials. They also require separation of the grafted chains on the carbon from the polymer chains which are formed in solution.

SUMMARY OF THE INVENTION

In order to overcome these limitations, the inventors have studied this problem and propose, in the present invention, a new process for the preparation of carbonated materials which are grafted with polymers, which consists of fixing at the surface of carbonated materials, polymer segments via ester or amide bonds by a mechanism of dehydration which is easy to implement.

The invention is also concerned with the application of these materials as an additive of electronic conduction in particular in electrochemical generators, as an anti-corrosive deposit and/or an electronic conductor on different Supports (plastic, aluminum, . . . ), and as inks, in particular offset inks.

DESCRIPTION OF THE INVENTION

The present invention proposes a new process enabling grafting of polymers bearing at least one carboxyl, hydroxyl or amine function, from carboxyl, amine or hydroxyl functions which are present at the surface of carbonaceous materials which are in the form of powders or fibres, the different possibilities being summarized in the reaction scheme given below. In this manner, a chemical bond is provided via an ester or amide bond.

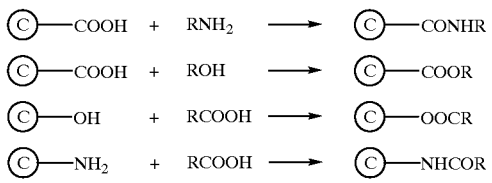

The novelty of this process resides in the fact that the reaction is carried out in such a manner that the carbon which is intended to be modified by polymer segments is in suspension in a solution containing the polymer which is intended to be grafted, and in the fact that the solvent is selected so as to be able to carry out the reaction of dehydration between a carboxyl function and an amine and/or an hydroxyl function at a suitable temperature.

Among the solvents, dimethylformamide or dimethyalcetamide are well suited for this type of reaction. They permit to dissolve a number of polymers and it was possible to show that the reaction was carried out within a few hours at temperatures of the order of 100–150° C. An alternative is offered by the utilization of a solvent which enables to carry an azeotropic distillation, such as chloroform, carbon tetrachloride, benzene, toluene, chlorobenzene or tetrachloroethane. These solvents enable to achieve the reaction of dehydration in a few hours, at the most at the boiling temperature of the solvent, i.e. for these four solvents at temperatures between 61 and 147° C.

Among functionalized carbons, carbons carrying amine functions are obtained by treating carbon fibres or powders with nitrogen containing gases (ammonia, amines, . . . ) such as described for example by Loskutov & Kuzin (*Synthesis and Properties of Ion-Exchange Materials,* (1968), Chmutov, K. V. ed., Moscow: Nauka, 95–101), however carbons carrying hydroxyl or carboxyl functions are more easily accessible, since they are easily obtained by oxidation and are available in the form of powders from different suppliers (Cabot, Columbian Carbon, Degussa, . . . ). Compound FW 200 of Degussa lends itself perfectly to this application because of the relatively important quantity of carboxyl groups at its surface, of the order of 0.6 mmoles/g.

Among polymers carrying at least one amine, carboxyl or hydroxyl function, copolymers having a single functionality and capable of reacting with the surface of carbon are preferred. Certain families are particularly interesting for this application and, in particular, polyoxyalkyleneamines commercially available from Huntsman under the name Jeffamine®), having a molecular weight between 600 and 2,100 g/mole (see Huntsman Technical Notice: "The Jeffamine® Polyoxyalkyleneamines"), polyoxyalkylene monoalcohols such as poly(ethylene glycol) methyl ether and polypropylene glycol) monobutyl ether, polyalkanesdiol monoalcohols. It is therefore possible to utilize a hydrophilic polymer selected for example from polyoxyalkylene monoamines, polyalkylene monoalcohols and polyalkanediol monoalcohols. A hydrophobic polymer selected from polyalkene monoalcohols such as polyethylene monoalcohol may also be used.

A special class of monoamine or monoalcohol is also of a wide practical interest. This class does not include polymers but monomers integrating an amine function or an alcohol function and a vinyl ether function (by extension excluding alkyl vinyl ethers which may be used in whole or in part to replace polymers). A monoamine under consideration particularly includes the vinyl ether of 3-amino-1-propanol and an alcohol of particular interest includes ethylene glycol vinyl ether, butanediol vinyl ether, cyclohexanedimethanol vinyl ether, diethylene glycol vinyl ether and hexanediol vinyl ether, which are commercially available from BASF. The carbon thus modified may thereafter be co-cross-linked with vinyl ethers or mono- or polyfunctional vinyl alkyl ethers and/or mono- or polyfunctional unsaturated monomers (maleimide, fumarate, . . . ) thus enabling integration of the carbon in a macromolecular network. Cross-linking with vinyl ethers or alkyl vinyl ethers may be initiated by activation of a photopolymerization initiator under the effect of actinic radiation, including β radiation. As photoinitiator, iodoniums, sulfoniums, phosphoniums, organo-metallic compounds capable of releasing an acid under the effect of actinic radiation may for example be mentioned. For example, an initiator that can be used includes substituted or non-substituted diaryls, substituted or non-substituted phenacyl-dialkyl sulfonium compounds, substituted or non-substituted areneferroceniums. Cross-lnking may also be carried out in the presence of a free radical initiator which releases radicals under the effect of heat, a phenomenon which is well known to one skilled in the art, or it may also be carried out after having formed the various components into thin films, which may be placed on a plastic, ceramic or metallic support. For example, the support may be aluminum, nickel or copper, or a sheet of polypropylene, polyethylene, polyethylene terephthalate, polyimide. Grafting of a vinyl ether function being more interesting than a number of other polymerizable groups, a polymerization involving a mechanism of the cationic type presents indeed a number of advantages. In particular, it is fast, even at low temperature, the rate of utilization of the monomer is high and sensitivity towards atmospheric contaminants such as oxygen, is low as compared to free radical or anionic polymerizations.

According to the preferred general process, a suspension of carbon carrying carboxyl functions in solution in toluene or benzene is treated by azeotropic distillation of the monofunctional polymer carrying an amine or hydroxyl function in stoichiometry. After 24 hours under reflux, the grafted carbon is recovered by filtration of the reaction mixture and dried. It may eventually be washed by stirring in a solvent such as pure ether or a mixture thereof with a co-solvent such as ethyl acetate for example. When the grafted carbon is soluble in benzene or toluene, it is recovered by reprecipitation of the reaction mixture in ether, filtration and drying.

There are thus obtained particles of carbon which are grafted with different polymer segments and in particular FW 200 grafted with Jeffamine® monoamine M-600 (≈600 g/mole), M-715, M-1000, M-2005, M-2070, with polyethylene monoalcohol with poly (propylene glycol) monobutyl ether, with poly(ethylene glycol) methyl ether, with 3-amino-1-propanol vinyl ether or with hexanediol vinyl ether.

Moreover, the inventors have succeeded in showing the interest of these carbonated material as additives of electronic conduction in electrochemical generators. As a matter of fact, the electrochemical systems should ensure within their electrodes a simultaneous transport of electrons and ions to permit the production of oxido-reduction reactions which are at the origin of their operation.

By way of simplification, and dealing only with electrochemical generators, it is well known for example that in alkali batteries $Zn/MnO_2$ or lithium batteries, the addition of an electronic conductor within the cathode is an essential element for their operation. This electronic conductor, mixed with the electroactive material and the binder to form a composite electrode, enables the generators to give an output power which is compatible with the proposed use for these systems.

The carbonaceous material which is more often used for this application is carbon black, such as Shawinigan black, in which the three dimensional arrangement in bead form ensures a high electronic conductivity to the composite for rates of addition of the order of 10% by volume. The carbons of the Ketjenblack® type of Akzo also enable to provide an important electronic conductivity to a composite, by dispersion within the latter. Contrary to Shawinigan black which has a low specific surface ($\approx 20$ m$^2$/g), these carbons have an important specific surface of 300 to 600 m$^2$/g. In this case, the high electronic conductivity induced by Ketjenblack® is associated with the specific morphology of the carbon particles in "shell" form. It is indeed well accepted that such a morphology enables to provide a high electronic conduction by tunnel effect between the different particles, without requiring an important structuralization of the carbon particles. Let us also mention as additive enabling an electronic conductivity, graphites of high specific surface sold by Lonza.

These carbonated materials fulfill their role in electrochemical generators, since the techniques used for their production enable production of composites capable of insuring the operation. In spite of this, these materials still present a number of disadvantages in terms of utilization.

Thus, all the carbon types described previously require the use of mechanical systems involving a relatively high shear strength to paste the materials of the cathode with carbon such as in Sn/MnO$_2$ batteries or to homogeneously disperse the composite mixture of insertion material, carbon and polymer in polymer electrolyte lithium batteries. Moreover, it is well known that the addition of carbon very rapidly increases the viscosity of polymer matrices containing them in amounts lower than 10% in volume, in the case of Ketjenblack® K600 for example. This generally leads to the appearance of a porosity at the cathode, which is detrimental to its density of volumic energy in particular in polymer electrolyte batteries. Moreover, carbon has an expanding effect in a polymer matrix which makes the extrusion of matrices containing it particularly difficult.

It has been possible to show that substituting carbons normally used in electrochemical generators with carbon powders grafted with a sufficient quantity of an adequate polymer was beneficial and solved the problems exposed above.

In particular, the performances of FW 200 grafted with Jeffamine® M-2070 (FW 200/J-2070), consisting for the most part of polyethylene oxide were evaluated. This material appears as a compact powder of shiny aspect which is easily dispersible in organic solvents, this aspect being characteristic of a total covering of the carbon surface with the polymer. By way of comparison, FW 200 grafted with Jeffamine® M-1000 (FW 200/J-1000) has a dull aspect.

First, the conductivity of a compact pastil of FW 200/J-2000 was determined. It is indeed currently accepted that a modification of the surface of carbon drastically decreases its conductivity. Surprisingly, the conductivity of a compact pastil of FW 200/J-2000 is $\approx 2 \times 10^{-2}$ $\Omega \cdot$cm$^{-1}$ or $\approx 50$ S$^{-1} \cdot$cm, which is comparable to the conductivity noted for many carbon fibres for example, while this material in fact contains a volume fraction of only 29% carbon.

Conversely, with a volume concentration of 29% in volume and taking into account the elevated specific surface of FW 200 which is higher than 300 m$^2$/g, it was surprising to realize that the pastil obtained had a homogeneous appearance and a good mechanical behaviour.

It was thus possible to produce composite cathodes for polymer electrolyte lithium batteries containing an insertion material, a derivative of polyoxyethylene and FW 200/J-2000 having no residual porosity contrary to a similar cathode utilizing Shawinigan black with the same volume fraction. It was also possible to produce a cathode directly by compaction of FW 200/J-2000 and an insertion material. This cathode had no residual porosity. With these cathodes, it was possible to produce lithium batteries having similar performances to the one utilizing Shawinigan black.

These materials are also useful as an additive of electronic conduction in anodes or cathodes or Li-Ion batteries utilizing carbon instead of lithium.

Moreover, it was possible to show that the extrusion of a matrix of polyoxyethylene containing FW 200/J-2000 and lithium bis(trifluoromethanesulfonyl)imide was much easier than the same matrix containing a volumic fraction of Shawinigan black The compound FW 200/J-2000 also has an undeniable practical interest for saline Zn/MnO$_2$ batteries. As a matter of fact, the decrease of water content of the cathode during discharge is a factor which limits the performances of these batteries. Now, the hydrophilic polyoxyethylene segments enable preservation of a sufficient hydration of the cathode during the entire discharge. The result is a better operation of these primary batteries.

Carbons which are grafted with polyoxyethylene chains are also interesting because of their good dispensability and the stability of the colloidal suspensions obtained as pigment in aqueous medium.

Carbons grafted with alkyl chains are particularly advantageous as additives in polymers with low polarity such as nitrile rubbers.

Carbons including polymerizable vinyl ether functions are particularly interesting for providing conductive deposits or for producing offset inks. It is thus possible to prepare suspensions of carbon containing vinyl ether functions in reactive solvents containing vinyl ether functions and also a photoinitiator. After having placed these suspensions on any kind of support, carbon deposits are obtained by irradiating the surface with a U.V. lamp. These deposits are particularly useful to provide protection against corrosion of the aluminum collectors used in liquid, gel or polymer electrolyte lithium batteries; solvents with low polarity which limit the diffusion of ions are then preferred. On the other hand, they can be used to prepare printing inks with rapid fixation following a U.V. radiation for offset processes. They can also be used to provide conductive deposits on lithium anodes which are used in polymer electrolyte lithium batteries.

The process which is used is versatile and it is also possible to obtain grafted carbons with different polymers or functions. It is thus possible to obtain for example FW 200 which is grafted in part with Jeffamine M-2000 and in part with 3-amino-1-propanol vinyl ether, thus enabling in final analysis co-cross-lining of this carbon with a reactive solvent or an adequate polymer matrix.

Moreover, it is of course obvious that the interest of this process extends to the grafting of polymers integrating in their chains any kind of functions such as redox couples, delocalized anions, metallic cations complexing molecules, molecules with optical properties.

The following examples serve to illustrate the operation of the present invention and the applications which result therefrom. They have no limiting character and one skilled in the art is free to conceive variants without departing from the scope of the invention.

BRIEF DESCRIPTION OF THE DRAWINGS

The invention is also illustrated without limitation by means of the annexed drawings, in which.

EXAMPLE 1

Figure 1:
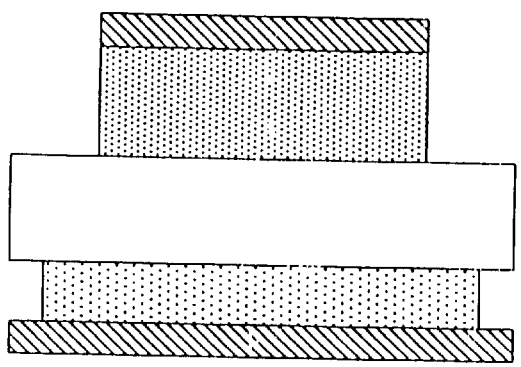
FIG. 1 illustrates an electrochemical generator incorporating a grafted carbon according to the invention.

To a suspension of 200 g of oxidized carbon, FW 200, (commercially available from Degussa), having 0.61 mmoles/g of carboxyl groups on its surface (122 mmoles of carboxyl groups), in 600 ml of toluene, there is added 136 g (122 mmoles) of a polyoxyalkylene monoamine, Jeffamine® M-1000 (J-1000, commercially available from Huntsman), with an average molecular weight of 1,116 g/mole. The molecular weight of Jeffamine® was determined by titration with hydrochloric acid. Previously, water and ammonia which are present in Jeffamine® were removed by bubbling dry argon at 60° C. during 24 hours. A measurement of the residual quantity of water by the Karl-Fischer titration method at less than 100 ppm has confirmed the validity of this process. An azeotropic distillation of the suspension was then carried out by maintaining stirring by means of an olive of magnetized Teflon®. After ≈30 mn, the solvent started to reflux in the Dean-Stark and after ≈10 mn, the appearance of the first drops of water was noted. After 20 hours under reflux, the quantity of water collected was ≈2.1 ml which agrees with the expected quantity (2.2 ml for the amidizing of 122 mmoles of —COOH) and it was noted that new water droplets ceased to appear. Reflux was maintained during 4 hours. After cooling, the reaction mixture was concentrated at 200 ml and poured into 1 l of ether. The grafted carbon was then recovered by filtration, and it was thereafter dried under vacuum.

An analysis of the material obtained by infrared spectroscopy with multiple reflection has confirmed the presence of an absorption band which is typical of amides and the disappearance of the band relative to the carboxyl groups which was noted on a reference spectrum of non-grafted oxidized carbon. On the other hand, a microanalysis of the grafted carbon has given a good conformity with the theoretical result (Table 1).

TABLE 1

Microanalysis of FW 200 grafted with Jeffamine ® M-1000

| Carbon | % C | % H | % O | % N |
| --- | --- | --- | --- | --- |
| FW 200 grafted J-1000 | 78.09 | 4.17 | 16.05 | 0.76 |
| Theoretical result (a) | 79.20 | 3.90 | 15.30 | 0.50 |

(a) Jeffamine ® M-1000 is believed to consist of 3 propylene oxide units for 19 ethylene oxide units (Huntsman Technical Notice: "The Jeffamine Polyoxyalkyleneamines).

This grafted carbon contains 40 weight percent of polymer and it is easily dispersed in organic solvents and water but a decanting of carbon after a few minutes is noted when sting of the dispersion is stopped.

EXAMPLE 2

According to a process similar to the one described in Example 1, 50 g of FW 200 (commercially available from Degussa), having 0.61 mmoles/g of carboxyl groups at its surface (30.5 mmoles of carboxyl groups) were reacted with 67.7 g (30.5 mmoles) of Jeffamine® M-2070 (J-2070, commercially available from Huntsman) having an average molecular weight of 2,219 g, purified and characterized such as described in Example 1. There is obtained a material of shiny aspect indicating that the surface was coated with Jeffamine® M-2070.

An analysis by infrared spectroscopy with multiple reflection has confirmed the grafting of Jeffamine® M-2070 with amide bonds. The result of a microanalysis of the grafted carbon confirms the theoretical result which is expected for this material.

TABLE 2

Microanalysis of FW 200 grafted with Jeffamine ® M-2070

| Carbon | % C | % H | % O | % N |
| --- | --- | --- | --- | --- |
| FW 200 grafted J-2070 | 73.10 | 4.90 | 21.30 | 0.78 |
| Theoretical result (a) | 73.40 | 5.50 | 19.50 | 0.40 |

(1) Jeffamine ® M-2070 is understood to be made of 10 propylene oxide units for 32 ethylene oxide units (Huntsman Technical Notice: "The Jeffamine Polyoxyalkyleneamines).

This grafted carbon contains 58 weight percent of polymer, and it is easily dispersed in organic solvents and water. The dispersions obtained are stable in time. It is thus possible to obtain an ink in an aqueous medium which is useful for ink or ballpoint pens.

EXAMPLE 3

To a suspension of 200 g of oxidized carbon, FW 200 of Degussa, having 0.61 meq/g of carboxylic groups at its surface (122 mmoles of carboxyl groups) in 300 ml of benzene, there is added 13.15 g (130 mmoles) of a monoamine vinyl ether, 3-amino-1-propanol vinyl ether CH=CHO $(CH_2)_3NH_2$ (commercially available from BASF). Then, the suspension is subjected to an azeotropic distillation by maintaining stirring with a magnetized Teflon® olive.

After ≈30 mn, the solvent started to reflux in the Dean-Stark and after ≈10 mn the appearance of the first drops of water was noted. After 14 hours under reflux, the quantity of water collected was ≈2.1 ml in accordance with the expected quantity (2.2 ml for amidizing of 122 meq of —COOH) and new drops of water have ceased to appear. Reflux was maintained during 2 hours. After cooling, the carbon grafted by filtration was recovered and it was thereafter dried under vacuum.

An analysis of the material obtained by infrared spectroscopy with multiple reflection has confirmed the presence of an absorption band which is typical of amides as well as a band of absorption which is typical of vinyl ethers and the disappearance of the band relative to carboxyl groups was noted on a reference spectrum of non-grafted oxidized carbon.

This grafted carbon may be co-cross-linked with mono- or polyfunctional vinyl ethers and/or unsaturated monomers (maleimide, fumarate, . . . ) thus enabling integration of the carbon into a macromolecular network.

EXAMPLE 4

By a process similar to the one described in Example 1, 164 g of FW 200 (100 mmoles of carboxyl groups) were reacted with 166.4 g (75 mmoles) of Jeffamine® M-2070 (J-2070) having an average molecular weight of 2,219 g, and which has been purified and characterized as described in Example 1, and 2.53 g (25 mmoles) of 3-amino-1-propanol vinyl ether (commercially available from BASF).

An analysis of the material obtained by infrared spectroscopy with multiple reflection has confirmed the presence of an absorption band which is typical of amides as well as an absorption band which is typical of vinyl ethers and the disappearance of the band relative to carboxyl groups noted on a reference spectrum of non-grafted oxidized carbon.

This material is particularly interesting since it contains grafted polymer segments of Jeffamine® M-2070 (50 weight percent) in a sufficient quantity to ensure an easy dispersion of the carbon and to give stable suspensions as well as vinyl ether functions enabling cross-liking of this carbon with mono- or polyfunctional vinyl ethers and/or unsaturated monomers (maleimide, fumarate, . . . ).

EXAMPLE 5

In a Nalgene flask, there is introduced 7 g (70 weight percent) of the grafted carbon obtained in Example 2 and 3 g (30 weight percent) of poly(ethylene oxide) of $M_W=3\times10^5$ and 50 ml of acetonitrile. Zirconia rolls were added and the flask was rotated on a shaft. After 24 hours, there is obtained a stable suspension of carbon in the poly(ethylene oxide) solution in acetonitrile. This suspension was then poured in a glass ring placed on a sheet of Teflon treated aluminum. During the time required to evaporate the solvent (about 24 hours), no sedimentation of the grafted carbon was observed. Once the solvent was evaporated, the film obtained was dried under vacuum during 48 hours. This film which in fact contains 29 weight percent of carbonaceous material (i.e. 20 weight percent) surprisingly has a very homogeneous aspect and an absence of porosity. It has an electronic conductivity higher than $10^{-3}$ $\Omega\cdot cm^{-1}$.

This result confirms the interest of the grafted carbons of the invention to produce composites in particular for the electrodes of polymer electrolyte lithium batteries.

EXAMPLE 6

A composite cathode was produced by co-crushing the grafted carbon obtained in Example 2 with vanadium oxide $V_2O_5$. Then, a compact and non-porous composite cathode was obtained by pressing under 2 tons. A pastil was then cut by stamping out and it was mounted on an electrochemical generator where it was used as cathode, the generator also including a polymer electrolyte based on polyoxyethylene having a molecular weight of $5\times10^6$ g/mole containing the lithium salt of bis(trifluoromethanesulfonyl)imide at a concentration O/Li=15/1 and a lithium anode. Stainless steel current collectors were then placed on each face as shown in FIG. 1.

Figure 2:
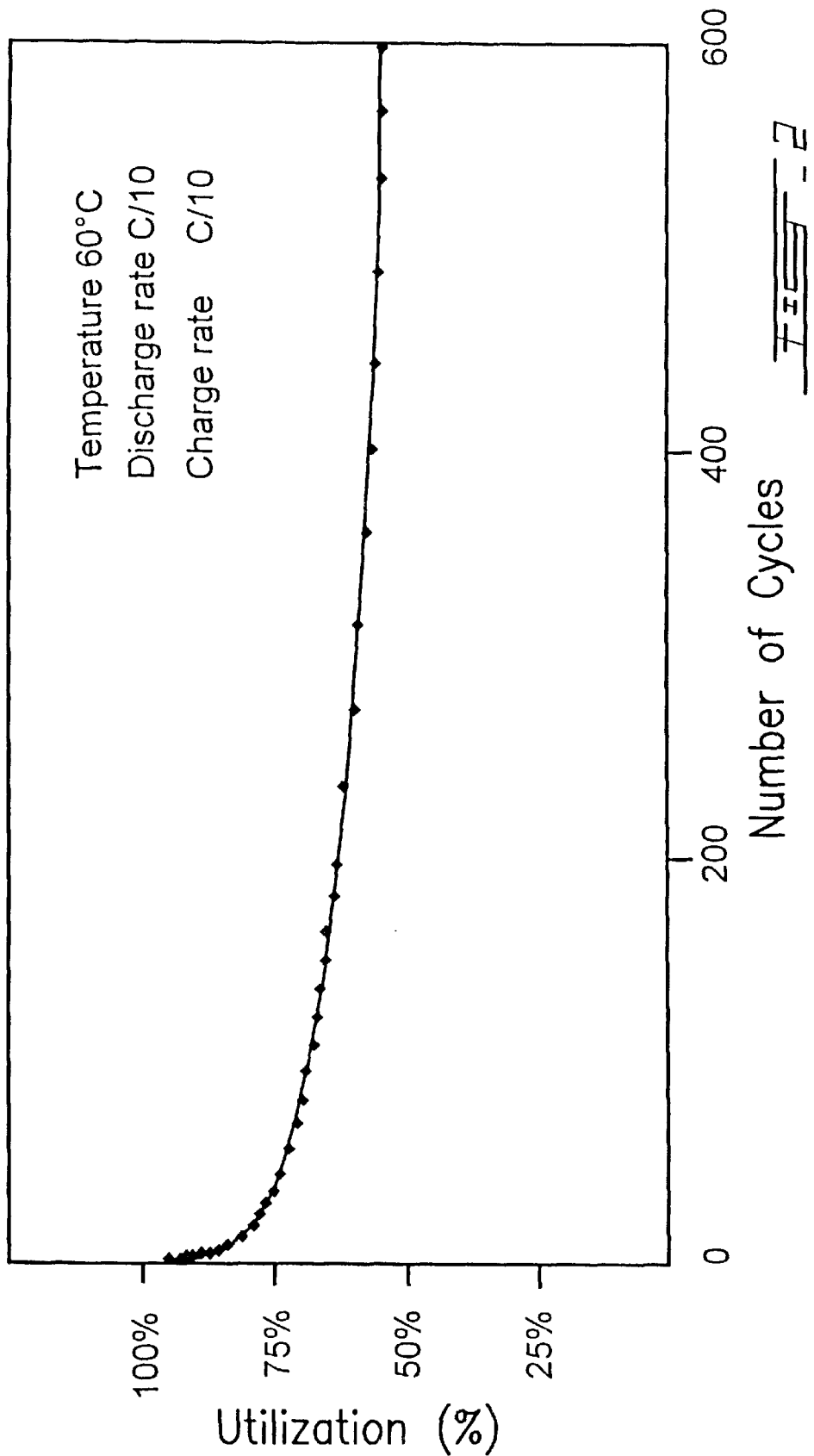
FIG. 2 is a cycling curve obtained with a generator according to FIG. 1.

The assembly was sealed in a pastil battery casing which enables to protect the generator from the atmosphere as well as to exert a mechanical strain of the film. This battery was then placed within an enclosure under argon placed in a dryer at a temperature of 60° C. It was then cycled between 1.8 and 3.3 V at a rate of charge and discharge of C/10 (nominal capacity charged or discharged in 10 hours). The cycling curve obtained under these conditions is given in FIG. 2.

This battery has given very good performances in cycling, thus after 600 cycles, there is still a capacity in discharge higher than 70% of the capacity at the tenth cycle. This result confirms the interest of the grafted carbon atoms of the present invention for polymer electrolyte lithium batteries.

EXAMPLE 7

In a Nalgene flask, there is introduced 7 g (70 weight percent) of the grafted carbon obtained in Example 4, 1 g (10 weight percent) of cyclohexanedimethanol vinyl diether (commercially available from BASF) and 2 g (20 weight percent) of octadecyl vinyl ether (commercially available from BASF) as well as 50 mg of the diphenyliodonium salt of bis(perfluorobutanesulfonyl)imide. After having added 20 ml of acetonitrile, the mixture was crushed with zirconia rolls as in Example 5.

After 24 hours, the suspension obtained was poured in a glove box under argon, in a glass ring placed on a sheet of previously cleaned aluminum 20 µm thick.

After four days in the glove box, the film was treated with U.V. radiation at 254 nm, at a power of 1,900 mW/cm² during 30 seconds, followed by a period of 10 mn enabling propagation of the species produced in the medium (postcure). There is finally obtained a film 11 µm thick on the sheet of aluminum, thereafter designated F1. Using the same principle, there is produced a deposit of grafted carbon (40 weight percent) such as obtained in Example 3 in a matrix of cyclohexanedimethanol vinyl diether (60 weight percent). There is thus obtained a film 8 µm thick on the sheet of aluminum, thereafter designated F2.

A first electrochemical generator was then prepared utilizing a composite cathode based on vanadium dioxide (45 weight percent), Shawinigan black (5% by volume) and polyethylene oxide (50 weight percent). A film was prepared from a suspension obtained under conditions similar to those described in Example 5. After drying under vacuum during 72 hours, a generator was assembled according to the same principle as the one described in Example 5, except that the composite of the present example was used as cathode and a sheet of aluminum covered with a deposit of carbon/polymer (F1) was used as a current collector.

Figure 3:
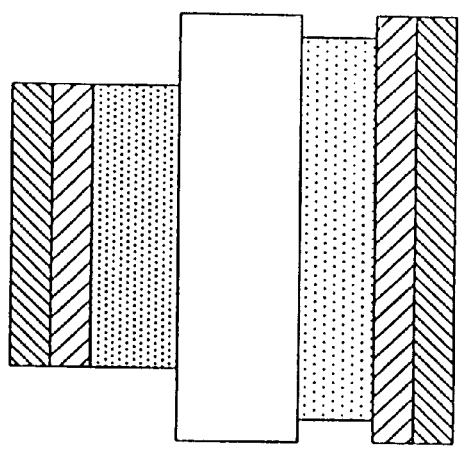
FIG. 3 illustrates an electrochemical generator incorporating another type of grafted carbon according to the invention.

A second electrochemical generator was prepared following the same principle except that a sheet of aluminum covered with a deposit of carbon/polymer (F2) was used as a current collector. Reference is made to FIG. 3.

According to the same principle, by way of comparison, a third electrochemical generator was prepared by using a previously cleaned blank sheet of aluminum.

Figure 4:
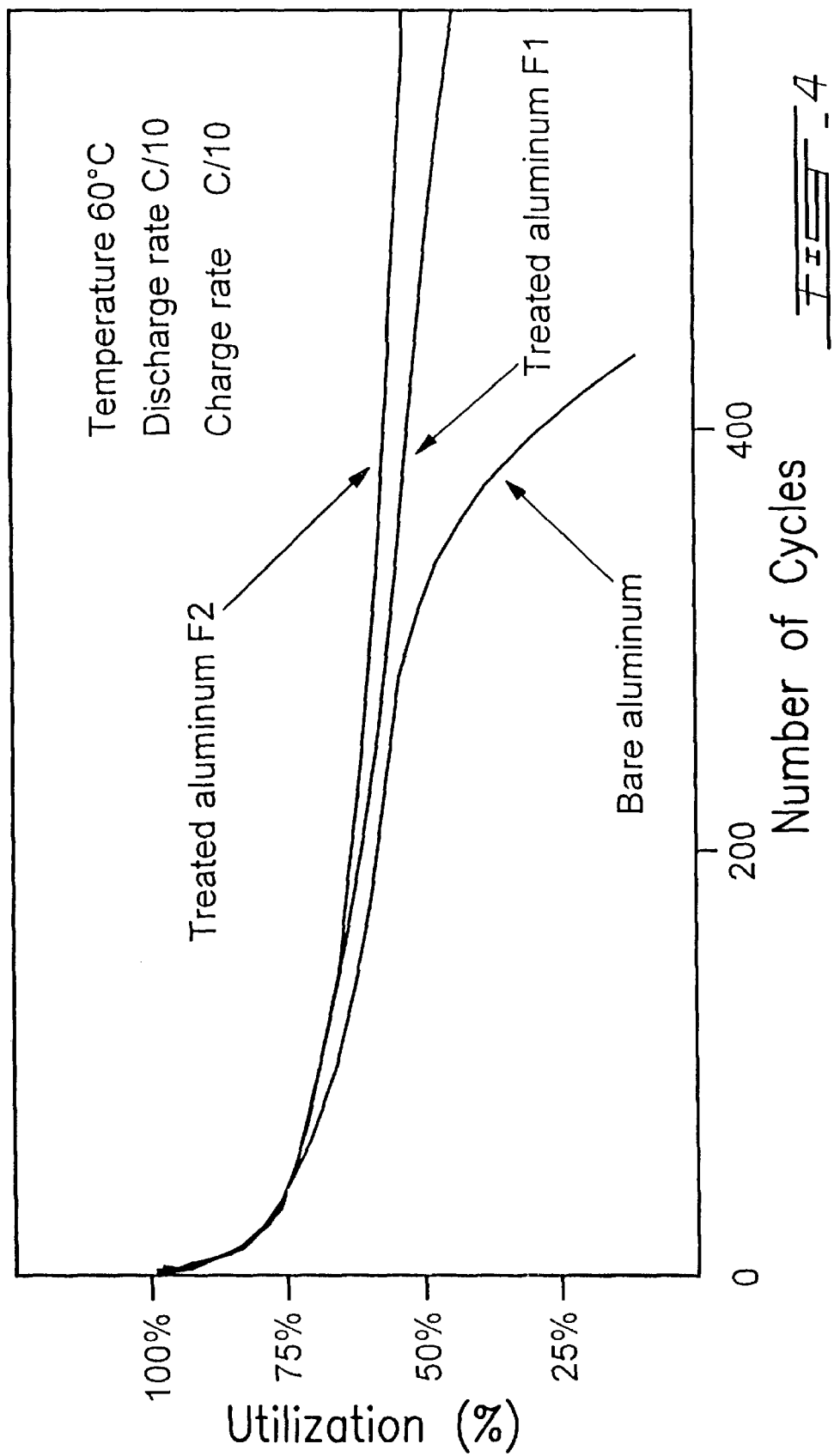
FIG. 4 is a cycling curve obtained with a generator according to FIG. 3.

These three generators were cycled under conditions similar to those described in Example 6. The curves of cycling obtained under these conditions are given in FIG. 4.

As perfectly illustrated in this example, the grafted carbons of the present invention are adapted to prepare anti-corrosive deposits in particular for current collectors of polymer electrolyte lithium batteries. The carbon deposit containing no polyethylene segments is still more performing for this application, since the low polarity and non-solvating character of the matrix used gives an even better protection against corrosion to the aluminum collector.

EXAMPLE 8

Three $Zn/MnO_2$ batteries of saline technology were prepared using an electrolyte made of an aqueous solution of ammonium chloride at a concentration of 1 M and a composite cathode made of 70% by volume of manganese dioxide $MnO_2$ and 30% by volume of the grafted carbon obtained in Example 2.

The first generator was discharged at a rate of discharge of C/10, the second was discharged by intermittence at a rate of C/10 during 1 hour followed by a pause of 24 hours and so forth. The third generator was placed in storage.

It was possible to note an improvement in the performances of these batteries as compared to standard batteries in particular during storage, self-discharge going from 20% to 5% by semester, and the capacity extracted from the battery being increased by more than 25% in intermittent regime.

EXAMPLE 9

There is prepared a stable colloidal dispersion of the grafted carbon obtained in Example 3 (3 weight percent) in poly-THF-divinyl ether of molecular weight 290 (96 weight percent) containing the di(dodecylphenyl)iodonium salt of bis(perfluorobutanesulfonyl)imide as a photoinitiator. This dispersion was layered on paper and exposed to U.V. radiation at 254 nm, and a power of 1,900 mW/cm$^2$ for a few seconds. The deposit solidified nearly instantaneously. Good results were also obtained by diluting this ink with water.

Such ink compositions are particularly interesting for offset printing, due to the absence of organic solvent in the process. Moreover, the polymerization speed is compatible.

EXAMPLE 10

There is prepared a solution of a nitrile rubber (96 weight percent) in dichloromethane in the presence of a carbon similar to the one grafted with polyethylene of molecular weight 800, obtained by a process similar to the one described in Example 1 by replacing Jeffamine® monoamine with a polyethylene monoalcohol of molecular weight 800 (commercially available from Aldrich). The grafted carbon is easily dispersible in this solvent. After pouring the viscous solution and drying, there is obtained a homogeneous dispersion of carbon in the polymer.

This polymer has a conductivity of $10^{-6}$ S·Cm$^{-1}$ and antistatic properties.

It is understood that modifications are possible without departing from the scope of the present invention as defined in the appended claims.

What is claimed is:

1. A process for grafting at least one polymer at the surface of a carbonaceous material, which comprises suspending a carbonaceous material containing carboxyl, amine and/or hydroxyl functions on its surface in a solution comprising a solvent, at least one polymer and/or monomer which dissolve in said solvent, said polymer containing at least one carboxyl, amine and/or hydroxyl function, said monomer containing an amine or alcohol function and a vinyl ether or alkyl vinyl ether function, and treating the solution thus obtained under conditions promoting a dehydration reaction between at least one carboxyl function, and at least one amine and/or hydroxyl function, so as to graft at least one of said polymers and/or monomers onto said carbonaceous material by means of ester or amide bonds, thereby forming a carbonaceous material grafted with at least one polymer and/or at least one monomer.

2. The process of claim 1, wherein the dehydration reaction is carried out by heating said carbonaceous material suspended in said solution.

3. The process of claim 1, wherein the solvent is selected from dimethylformamide, dimethylacetamide, tetrachloroethane, carbon tetrachloride, chloroform, benzene, toluene and chlorobenzene.

4. The process of claim 3, wherein said carbonaceous material suspended in said solution is heated at a temperature between 60–150° C.

5. The process of claim 1, wherein the solvent is selected from dimethylformamide and dimethylacetamide, and the dehydration reaction is carried out by heating the suspension of carbonaceous material in said solution at a temperature of 100–150° C.

6. The process of claim 1, wherein the solvent is selected from carbon tetrachloride, chloroform, benzene, toluene, chlorobenzene, and tetrachloroethane, and the dehydration reaction is carried out by azeotropic distillation of the suspension of carbonaceous material in said solution.

7. The process of claim 6, wherein the azeotropic distillation is carried out at less than or equal to the boiling temperature of said solvent.

8. The process of claim 1, wherein said polymer carries a single function selected from the group consisting of carboxyl, amine and hydroxy functions.

9. The process of claim 1, wherein said polymer is a hydrophilic polymer selected from polyoxyalkylene monoamines, polyoxyalkylene monoalcohols, and polyalkane diols.

10. The process of claim 8, wherein said polymer is a hydrophobic polymer selected from polyalkene monoalcohols.

11. The process of claim 9, wherein said polymer is selected from polyoxyalkylene amines, poly(ethylene glycol) methyl ether, and poly(propylene glycol) monobutyl ether.

12. The process of claim 10, wherein said polymer is a polyethylene monoalcohol.

13. The process of claim 1, wherein said solution comprises said monomer.

14. The process of claim 1, wherein said solution comprises said polymer and said monomer.

15. The process of claim 13, wherein the monomer is selected from 3-amino-1-propanol, ethylene glycol vinyl ether, butanediol vinyl ether, cyclohexanedimethanol vinyl ether, diethyleneglycol vinyl ether and hexanediol vinyl ether.

16. The process of claim 13, wherein said carbonaceous material which has been grafted with at least one polymer at its surface is cross-linked with mono- or polyfunctional vinyl ethers.

17. The process of claim 13, wherein said carbonaceous material which has been grafted with at least one polymer at its surface is cross-linked with mono- or polyfunctional vinyl ethers or alkyl vinyl ethers and mono- or polyfunctional unsaturated monomers.

18. The process of claim 16, wherein the cross-linking with vinyl ethers or alkyl vinyl ethers is initiated by activation of a photopolymerization initiator under actinic radiation, including β radiation.

19. The process of claim 18, wherein the photoinitiator is selected from the group consisting of iodonium compounds, sulfonium compounds, phosphonium compounds, and organometallic compounds enabling release of an acid under the effect of actinic radiation.

20. The process of claim 19, wherein the photoinitiator is selected from substituted or nonsubstituted diaryliodonium compounds, substituted or non-substituted phenacyl-dialkylsunfonium compounds, and substituted or non-substituted arene-ferrocenium compounds.

21. The press of claim 17, wherein the cross-linking is carried out in the presence of a free radical initiator which releases radicals under the effect of heat.

22. The process of claim 16, wherein the cross-linking is carried out after forming the grafted carbonaceous material in the form of a thin film.

23. The process of claim 22, wherein the thin film is placed on a plastic, ceramic or metallic support.

24. The process of claim 23, wherein the support comprises aluminum, nickel, zinc, lithium or copper.

25. The process of claim 23, wherein the support is a sheet of polypropylene, polyethylene, polyethyleneterephthalate, polyimide, polyacrylonitrile, polyvinylchloride, polyester, polyether, nylon, polyvinylacetate, polystyrene, methylpolymethacrylate, polybutadiene, polyisoprene, or polyamide.

26. The process of claim 1, wherein the carbonaceous material is carbon black.

27. The process of claim 13, wherein said monomer comprises an amine function or an alcohol function.

28. The process of claim 14 wherein the monomer is selected from the group consisting of 3-amino-1-propanol, ethylene glycol vinyl ether, butanediol ether, cyclohexanedimethanol vinyl ether, diethylene glycol vinyl ether and hexane diol vinyl ether.

29. The process of claim 14, wherein the carbonaceous material which has been grafted with said polymer and said monomer at its surface is cross-linked with a mono- or polyfunctional vinyl ether or alkyl vinyl ether.

30. The process of claim 14, wherein the carbonaceous material which has been grafted with said polymer and said monomer at its surface is cross-linked with mono- or polyfunctional vinyl ethers or alkyl vinyl ethers or mono- or polyfunctional unsaturated monomers.

* * * * *